US012337067B2

United States Patent
Houtz, II

(10) Patent No.: US 12,337,067 B2
(45) Date of Patent: Jun. 24, 2025

(54) ORAL MEDICINE DELIVERY CAPSULE

(71) Applicant: Don S. Houtz, II, Elko, NV (US)

(72) Inventor: Don S. Houtz, II, Elko, NV (US)

(*) Notice: Subject to any disclaimer, the term of this patent is extended or adjusted under 35 U.S.C. 154(b) by 0 days.

(21) Appl. No.: 18/299,658

(22) Filed: Apr. 12, 2023

(65) Prior Publication Data
US 2023/0240996 A1 Aug. 3, 2023

Related U.S. Application Data

(62) Division of application No. 16/688,924, filed on Nov. 19, 2019, now abandoned.

(60) Provisional application No. 62/770,607, filed on Nov. 21, 2018.

(51) Int. Cl.
A61K 9/48 (2006.01)
A61K 9/00 (2006.01)

(52) U.S. Cl.
CPC .......... *A61K 9/4825* (2013.01); *A61K 9/0056* (2013.01); *A61K 9/4808* (2013.01)

(58) Field of Classification Search
CPC .............................. A61K 9/4825; A61K 9/0056
See application file for complete search history.

(56) References Cited

U.S. PATENT DOCUMENTS 5,362,496 A * 11/1994 Baker .................. A61K 9/7084
424/443
2007/0218133 A1* 9/2007 Walker ..................... C12H 1/14
424/468

OTHER PUBLICATIONS

Thrombre I (Asymmetric membrane capsules for osmotic drug delivery: I. Development of a manufacturing process, Journal of Controlled Release, vol. 57, Issue 1, Jan. 1, 1999, pp. 55-64). (Year: 1999).*
Thrombre II (Asymmetric membrane capsules for osmotic drug delivery II. In vitro and in vivo drug release performance, Journal of Controlled Release, vol. 57, Issue 1, Jan. 1, 1999, pp. 65-73) (Year: 1999).*
Patel (Development of Osmotically Controlled Mucoadhesive Cup-Core (OCMC) Tablet for The Anti-Inflammatory Activity, I. Iran J Pharm Res. 2010 Winter; 9(1): 21-26). (Year: 2010).*

* cited by examiner

Primary Examiner — Benjamin J Packard

(57) ABSTRACT

An improved oral medicine delivery capsule may feature a gelled medicine contained within a carrier capsule designed to maintain its position in the oral cavity of a patient. A port covered with a mesh or other osmotic material allows the medicine to leach through to the oral tissues. Construction may be any known or later developed formulation which balances the need to contain and control the flow of medicine with durability in the oral cavity.

2 Claims, 8 Drawing Sheets

ORAL MEDICINE DELIVERY CAPSULE

CROSS-REFERENCES TO RELATED APPLICATIONS

This application claims priority as a divisional of U.S. application Ser. No. 16/688,924, filed Nov. 19, 2021, which in turn claims priority as a non-provisional perfection of U.S. App. No. 62/770,607, filed Nov. 21, 2018, and incorporates both applications by reference in their entirety herein.

FIELD OF THE INVENTION

The present invention relates to the field of medicine and more particularly relates to a capsule for targeted delivery of medicines to the oral cavity.

BACKGROUND OF THE INVENTION

The delivery of medicine to the body is accomplished by two simple concepts: either apply the medicine to the afflicted area or apply it at some other location so that it may be absorbed by the bloodstream and distributed to the afflicted area. Often medicines may be delivered orally—swallowed—and medicine is absorbed through either the stomach walls or small intestine. Unfortunately, most medicines do not survive the body's digestive system well and the dose must be increased to compensate for losses in the body. Alternatively, or tangentially, carriers must be developed which allow the medicine to traverse the digestive system. Sometimes these carriers may have their own side-effects. Then, after passing through the digestive system and being absorbed by the bloodstream, the medicine must be transported through the bloodstream, and distributed to the entire body, in order to provide the desired effect on the afflicted body part.

More efficient means of medicine delivery can include suppositories in the rectum or delivery thought the oral tissues. Both body parts have tremendous absorbing power and medicines absorbed in these locations then proceed directly into the blood stream so that medicine is not lost in the digestive system. However, while the suppository is an efficient delivery system for rectal use, no similar system is available for oral use. The oral environment is primarily designed to provide initial digestion of a person's food and therefore tends to soften and dissolve any suitable object put into it. Such dissolved medicines would then travel into the stomach and be greatly diminished by the digestive process described before. The calculation and planning for the digestive process also takes significant research and development on the part of pharmaceutical companies. What is needed then is an oral delivery system which protects contained medicine from being dissolved while also keeping it in position to be absorbed by the buccal and/or lingual oral surfaces without salivary dilution. The present invention is a capsule which contains medicine and is held in the oral cavity, such as against the gums or cheek, so that medicine may be absorbed through oral tissues into the blood stream directly. Of particular note, if the afflicted area is in the oral cavity (such as from a tooth extraction), medicine could be directly and topically delivered to the area by utilizing the present invention.

SUMMARY OF THE INVENTION

In view of the foregoing disadvantages inherent in the known types of medicine delivery systems, an improved medicine capsule may provide a delivery system that meets the following objectives: it is cost effective to manufacture, stow, and carry, being safe in the event of being swallowed, intuitive in its use, and providing targeted medicine to and/or through the oral cavity. This would not only bypass the digestive system (eliminating significant research and development costs and potential side-effects from carriers), but also not require any injections. As such, a new and improved medicine delivery system may comprise an outer capsule surrounding a gel medicine. The outer capsule may have an opening, which may be covered by a mesh or osmotic membrane, to allow medicine to seep out of the capsule and onto the oral surfaces.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also, it is to be understood that the phraseology and terminology employed herein are for description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

With reference now to the drawings, a preferred embodiment of the medicine delivery capsule is herein described. It should be noted that the articles "a", "an", and "the", as used in this specification, include plural referents unless the content clearly dictates otherwise.

Figure 1:
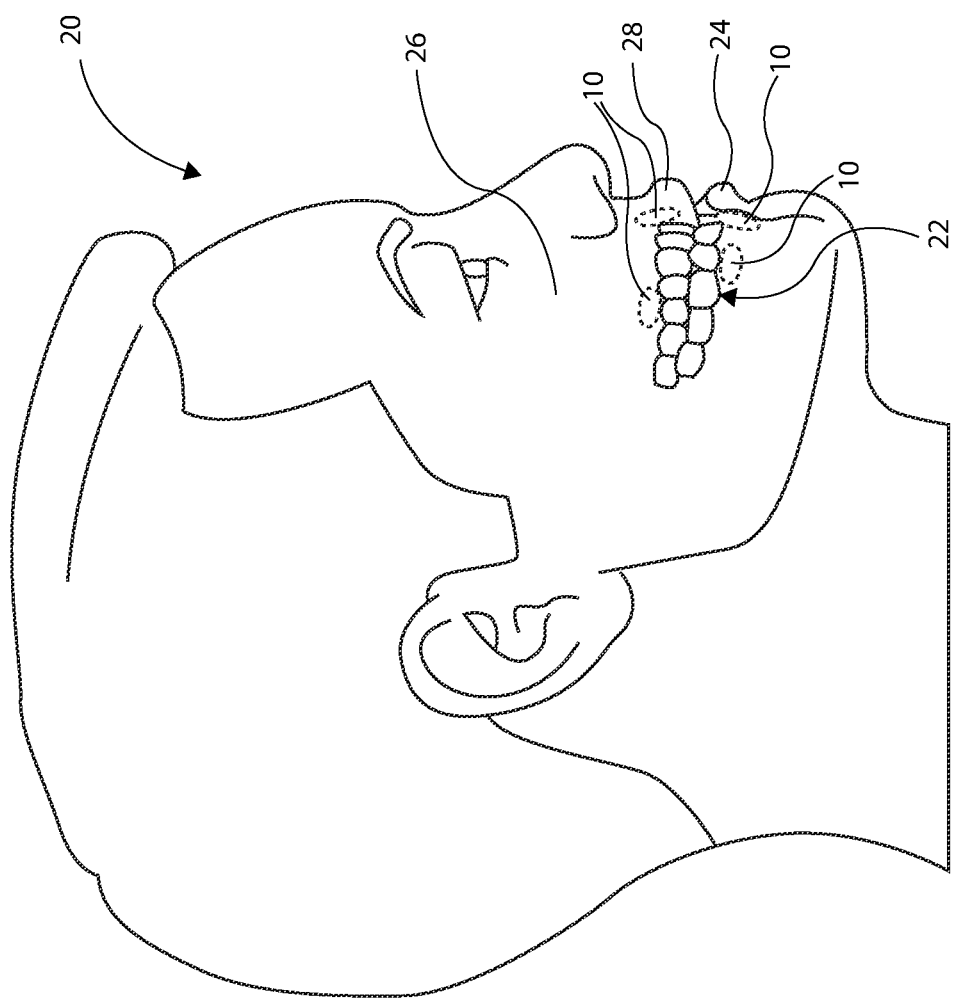
FIG. 1 is a side elevation, in partial transparency, of an individual showing use of one embodiment of the invention in multiple locations.
Figure 2:
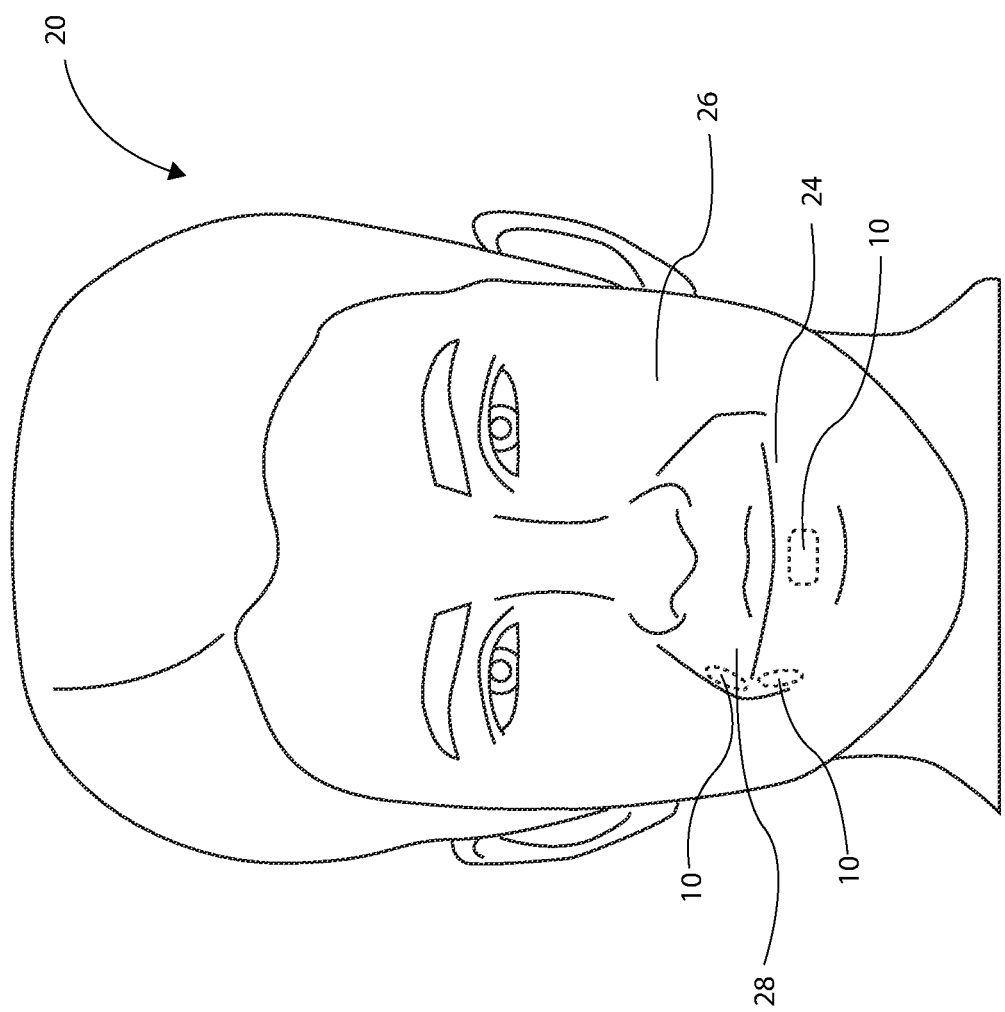
FIG. 2 is a front elevation of the individual of FIG. 1
Figure 3:
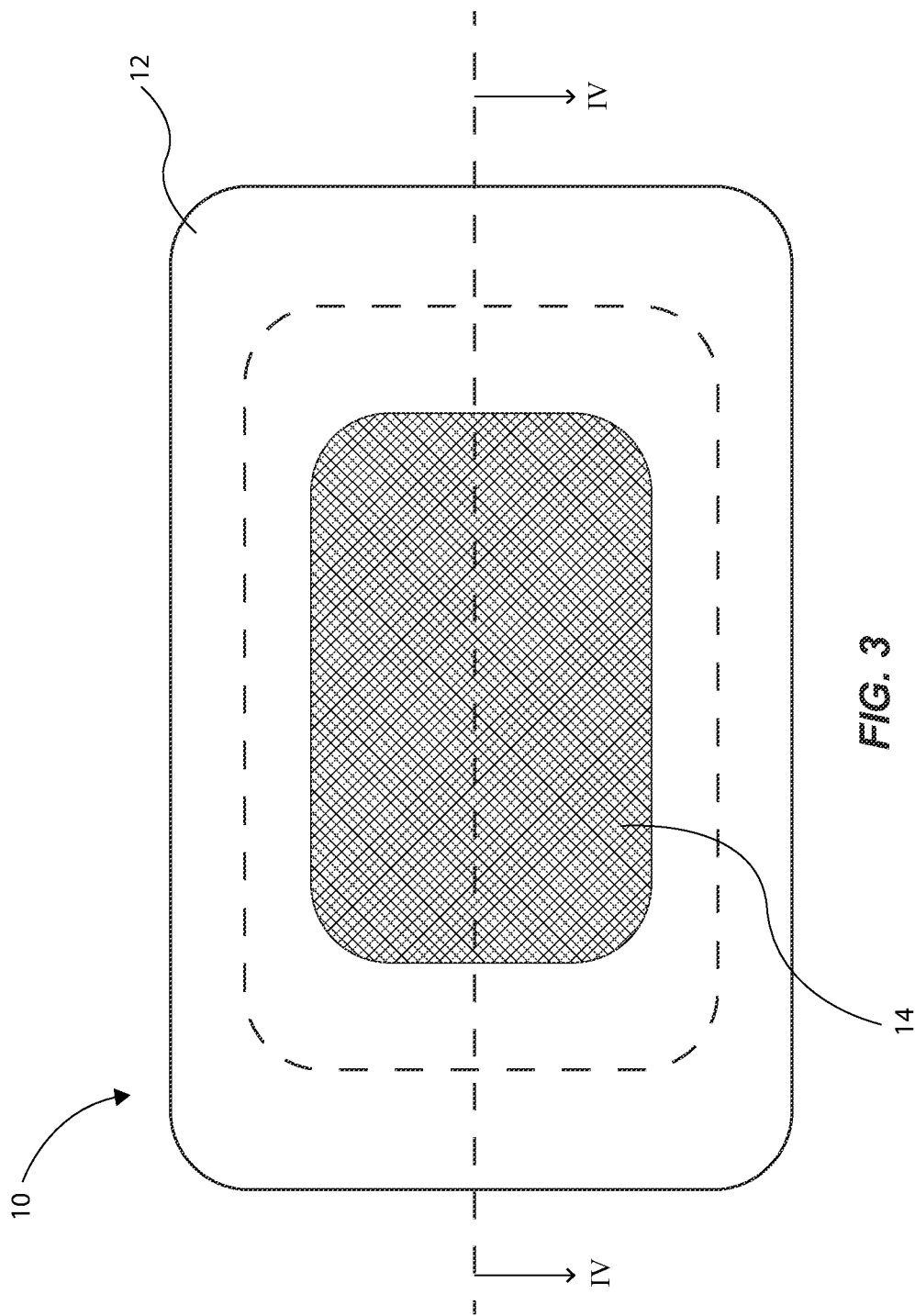
FIG. 3 is a top plan view of one embodiment of a capsule as an embodiment of the invention, opened.
Figure 4:
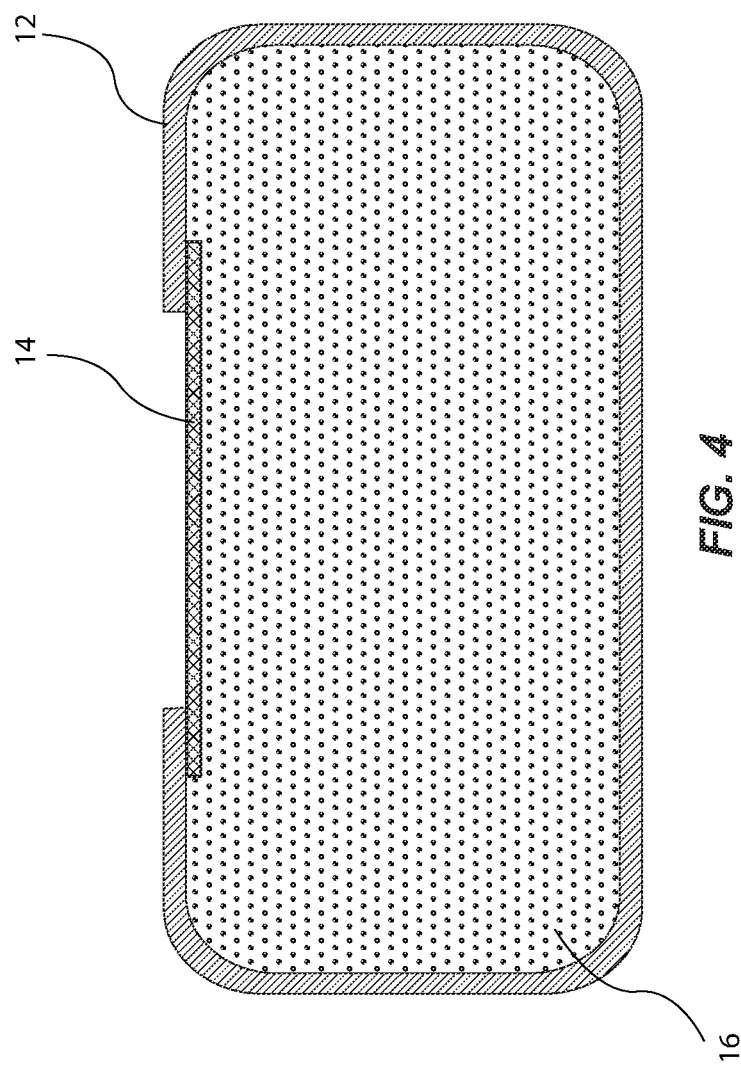
FIG. 4 is a sectional view of the capsule of FIG. 3, taken along line IV-IV.
Figure 5:
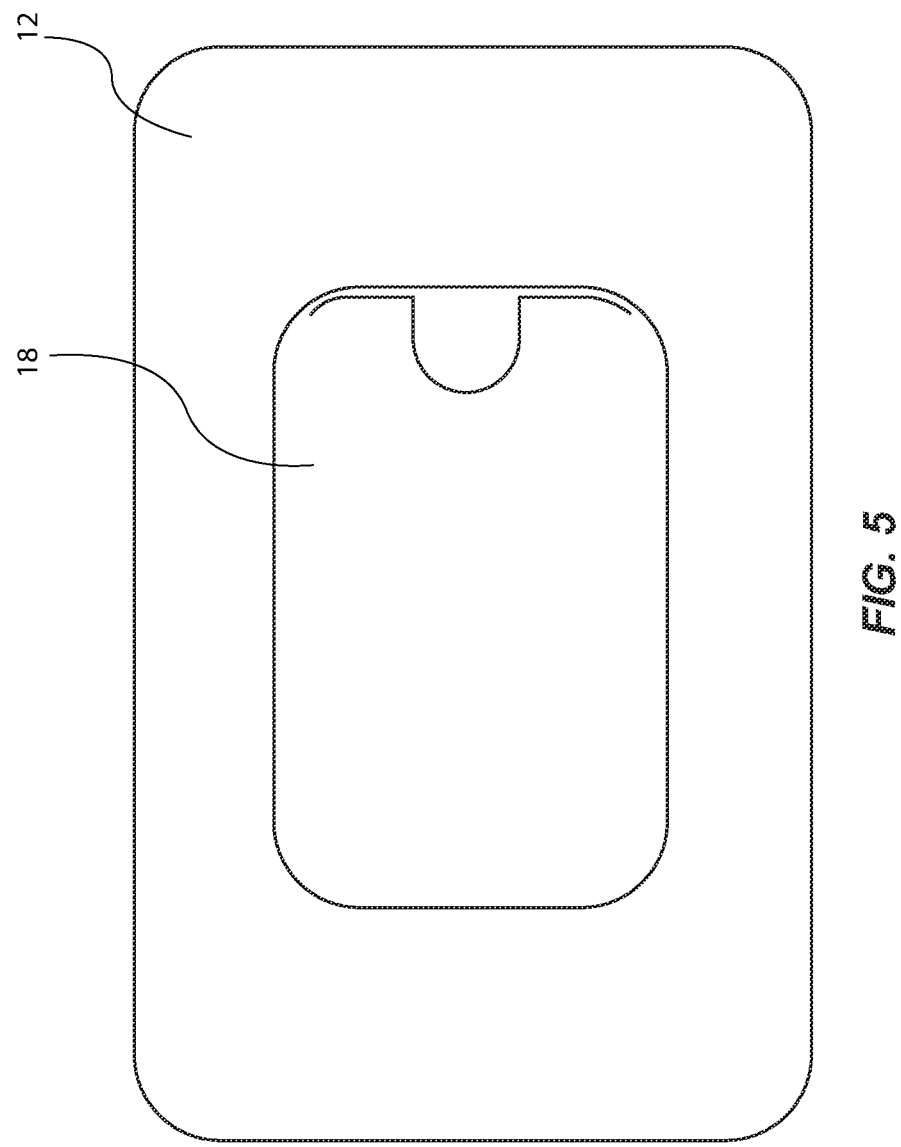
FIG. 5 is a top plan view of the capsule of FIG. 3, unopened.
Figure 6:
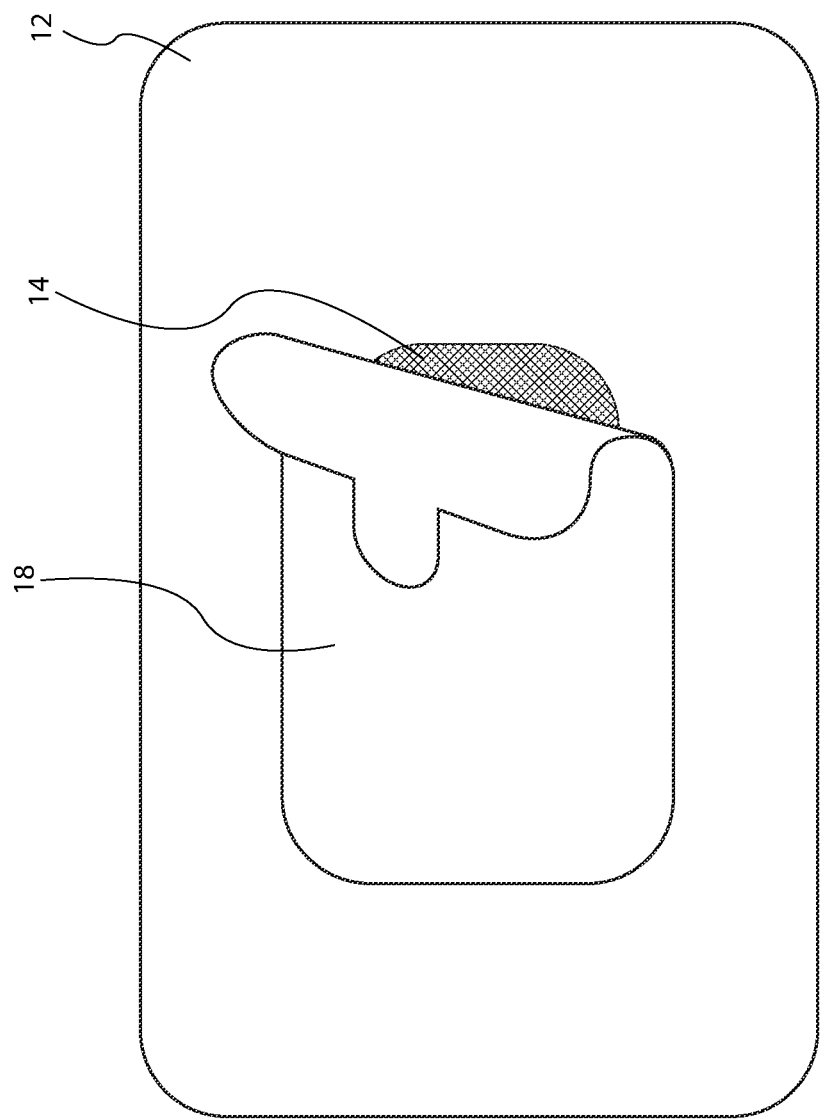
FIG. 6 is a top plan view of the capsule of FIG. 3, being opened.
Figure 7:
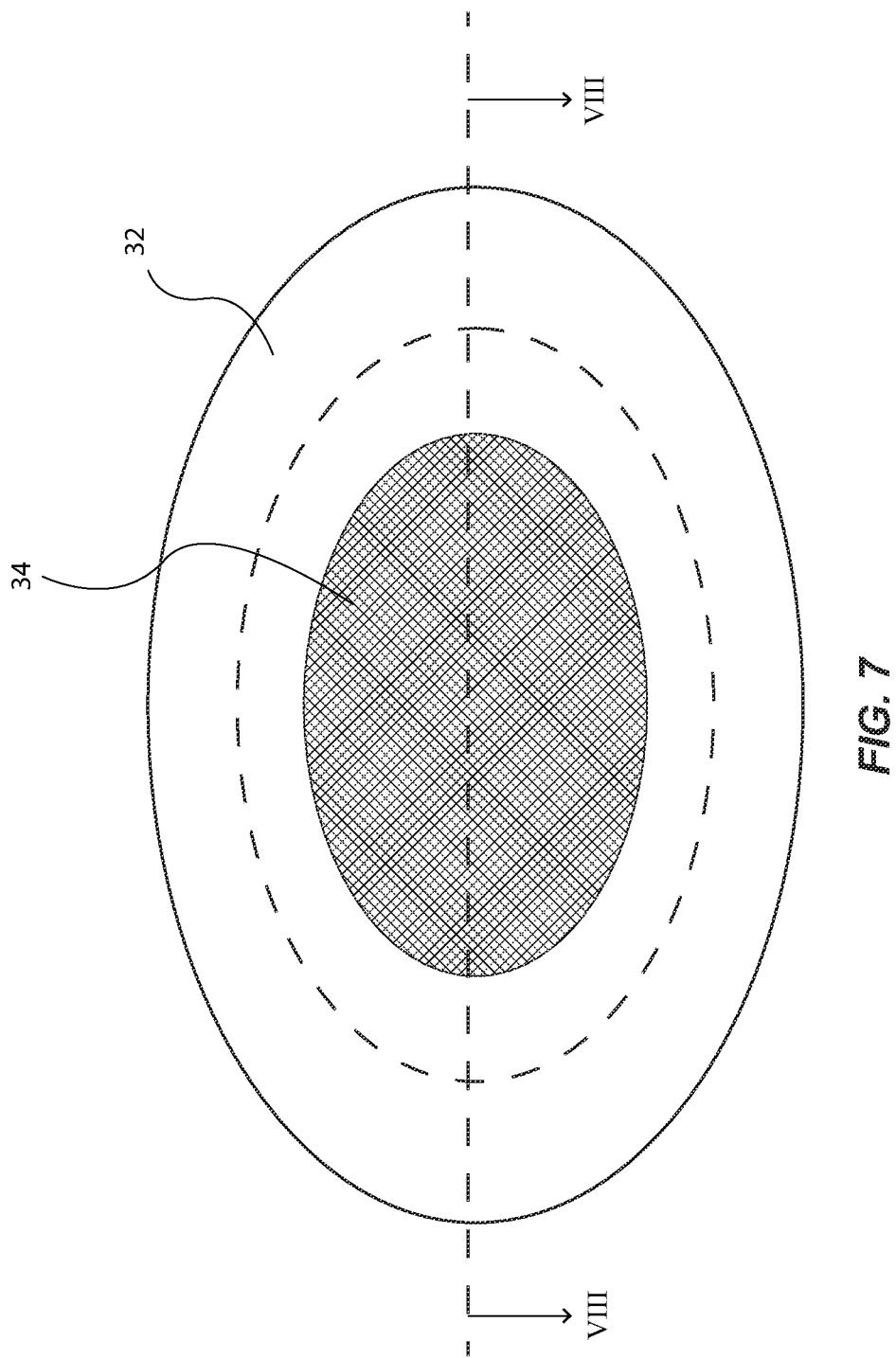
FIG. 7 is a top plan view of a capsule as an alternate embodiment to the invention.
Figure 8:
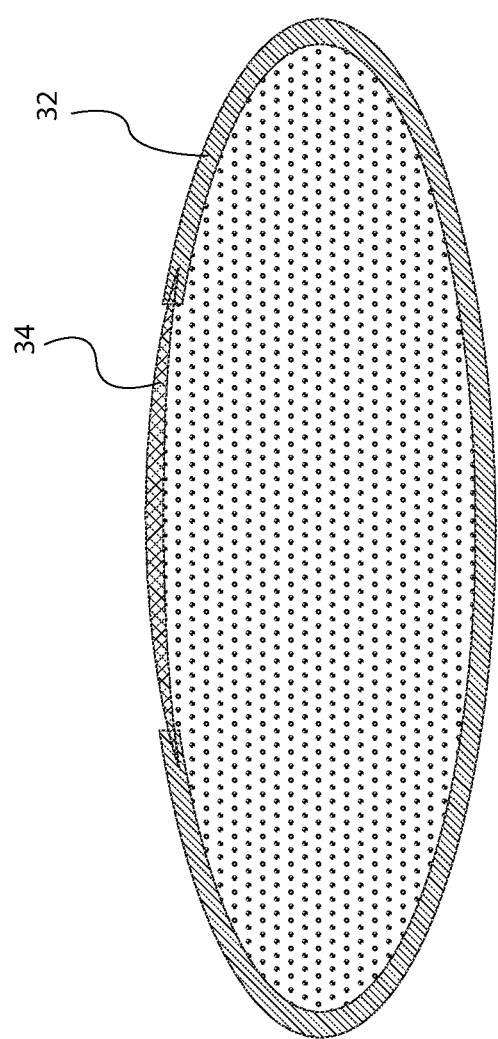
FIG. 8 is a sectional view of the capsule of FIG. 7, taken along line VIII-VIII.

With reference to FIGS. 1 and 2, a user 20 may place a capsule 10 in an area in the oral cavity, proximate the gumline 22 and lip 24 or cheek 26. The capsule 10 features an outer shell 12 with an opening covered by a mesh 14 (FIG. 3). Inside the capsule 12 is a medicine 16 that is usually in a gel formulation (FIG. 4), but may be dispersed in some other delivery medium, such as an oil. It should be understood that the purpose of the mesh 14 is to hold the medicine 16 within the opening and allow it to leach out of the capsule 12 during use in a time-controlled manner. Therefore, while the term "mesh" is primarily used in this application, the term should be construed to include any osmotic material which will allow passage of medicine through itself an into the user. The mesh thickness and size of its openings or the degree of osmotic activity that the osmotic material may allow would also be dependent upon the delivery medium. The opening and mesh are usually covered by a release liner 18 when stored. Said release liner 18 may be removed (FIGS. 5 and 6) for individual use. The mesh 14 may reside on an inner wall of the outer shell 12 (FIG. 4) or mesh 34 may be anchored within the capsule outer shell itself 32 (FIGS. 7 and 8).

In use, the capsule 10 is positioned in the oral cavity of the patient (FIG. 1). Positioning may be wherever it would make sense to position the capsule 10. FIG. 1 depicts use between the upper 28 or lower lip 24 and the buccal side of the gum line 22, but any position is possible, including between the gumline 22 and cheek 26. It is currently preferred that the medicine be a gel 16 because a gel may then slowly dissolve when in the oral cavity in order that medicine may leach out of the capsule and be absorbed by oral tissues. However, the choice of delivery medium would be dependent upon many different factors, including but not limited to the medicine itself and how it will interact with various media, activation time, cost, and general preference. The capsule outer wall 12 protects the medicine 16 from being dissolved too rapidly and may soften while in the oral environment so that it may be at least partially collapsible, so the patient may intentionally force medicine out of the capsule 10.

The outer shell 12 may be constituted of any suitable material. Currently most capsules are either maid from gelatin or vegetable products. Gelatin capsules are typically made from gelatin, glycerin, and purified water in varying proportions to achieve a desired consistency, resilience, and survivability in the digestive system. Vegetable capsules are typically constituted from hypromellose (a polymer constructed from cellulose) and pullulan (a polysaccharide polymer made from tapioca starch). All of these materials are already FDA approved and deemed safe in the event the capsule is accidentally, or intentionally, swallowed.

The mesh may be made of any known surgical mesh which is deemed safe for the body, in particular the digestive system in the event of swallowing. Such meshes may include nylons, polyesters, or other polymers which are also FDA approved. Osmotic membranes may also be utilized, assuming the requisite agency approval.

The size of the capsule 10 may vary according to the desired medicine containment. However, it will always be limited to what can be comfortably held in the oral cavity. Currently a capsule having dimensions of 1.91×0.95×0.64 cm (¾×⅜×¼ in) is envisioned as a starting point. The shape of the capsule and associated dimensions is not particularly relevant and both ovular and rectangular shaped capsules are contemplated (FIGS. 3 and 7).

The making of medicine gels is known in the art as they are active ingredients contained within a colloidal gel carrier. This colloidal gel carrier may be manufactured to any desired specification. Any active ingredient now known or later discovered which is suitable for making into a gel may be utilized within the invention.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A method of delivering medicine to an oral cavity, the method comprising:
    (a) a first step of encapsulating a medicine in a capsule having a shell which protects said medicine from being dissolved, said capsule also having an opening which is covered by a mesh which holds the medicine within the opening, and wherein said mesh resides on an inner wall of the shell or is anchored within the shell itself;
    (b) a further step of positioning the capsule in an oral cavity, against a surface of said oral cavity; and
    (c) maintaining the capsule on the surface of the oral cavity so that said medicine is absorbed by said surface.

2. The method of claim 1, the medicine being suspended in a colloidal gel carrier.

* * * * *